United States Patent [19]

Manley

[11] 4,340,045
[45] Jul. 20, 1982

[54] LUNG VENTILATOR

[75] Inventor: Roger E. W. Manley, Farnham Common, England

[73] Assignee: Compair Maxam Limited, Cornwall, England

[21] Appl. No.: 177,831

[22] Filed: Aug. 13, 1980

[30] Foreign Application Priority Data

Sep. 25, 1979 [GB] United Kingdom ............... 7933238
Nov. 27, 1979 [GB] United Kingdom ............... 7940968

[51] Int. Cl.³ .................................. A61M 16/00
[52] U.S. Cl. .......................... 128/204.24; 128/204.26; 128/205.24
[58] Field of Search ............... 128/204.21, 204.23, 128/204.24, 204.25, 204.26, 205.24

[56] References Cited

U.S. PATENT DOCUMENTS

| 3,910,270 | 10/1975 | Stewart | 128/204.24 |
| 3,976,064 | 8/1976 | Wood et al. | 128/204.23 |
| 4,098,272 | 7/1978 | Stewart | 128/204.24 |
| 4,121,579 | 10/1978 | Bird | 128/204.25 |
| 4,206,754 | 6/1980 | Cox et al. | 128/204.26 |
| 4,281,651 | 8/1981 | Cox | 128/204.23 |

FOREIGN PATENT DOCUMENTS 1576118 10/1980 United Kingdom ........... 128/204.23

OTHER PUBLICATIONS

"Soviet Inventions Illustrated" Week B18, Jun. 14, 1979, Section P33 and SU-A-611-616.

Primary Examiner—Henry J. Recla
Attorney, Agent, or Firm—Trexler, Bushnell & Wolters, Ltd.

[57] ABSTRACT

A lung ventilator which changes over automatically to provide either ventilation or to allow for natural breathing has an oxygen inlet (1) connected through a pressure regulator (2) and a flow regulator (4) to a reservoir (7). A secondary supply to the reservoir (7) takes place through a NOT unit (10). Oxygen from the reservoir (7) is supplied to a face mask connection (29) either through a demand valve (34) or through a second flow regulator (18) and a spool valve (26). The spool valve (26) is controlled by a pneumatic timing system (20–25) and the oxygen from the reservoir either flows intermittently through the spool valve (26) which is opened and closed by the timing system to provide ventilation or, it is supplied through the demand valve (34). Changeover from one supply to the other and back again is controlled in dependence upon the pressure in the reservoir (7). When there is a demand supply through the valve (34), this is greater than the gas supply through the regulator (4) and in consequence when the pressure in the reservoir (7) falls to a predetermined minimum value, the NOT unit (10) opens to provide an increased oxygen flow to the reservoir.

14 Claims, 2 Drawing Figures

LUNG VENTILATOR

This invention relates to lung ventilators, which are particularly intended for resuscitation purposes, but which may also be used in intensive care units.

Existing ventilators which are used for resuscitation provide a supply of oxygen or other respirable gas to a face mask and face valve under the control of a shut-off valve which is intermittently opened. In this way pulses of gas are supplied to the face mask to inflate the lungs of the person being resuscitated and during the time that the supply of gas is shut-off the lungs deflate again through the face valve. The rate of inspiratory flow is controlled by a flow regulator and this flow is at a predetermined minimum rate which may be less than the demand rate for gas if natural breathing starts. What is more, if natural breathing starts, it is likely that this will not be in phase with the pulses of gas supplied by the shut-off valve and an intake of gas by natural expansion of the lungs cannot of course take place while the shut-off valve is closed.

It is necessary therefore for the operator of the ventilator to observe the person whose lungs are being ventilated very closely and if natural breathing starts, the face mask of the ventilator must at once be removed. Natural breathing can then take place in the ambient atmosphere but only, of course, if the ambient temperature is of respirable gas. Natural breathing cannot take place from the ambient surroundings under water, or, for example, in a mine which is heavily contaminated with methane or in a building which may have been flooded with carbon dioxide for fire extinguishing purposes. Under these circumstances it is necessary for the operator of the ventilator to substitute a face mask provided with a demand supply of gas for the face mask of the ventilator and this change over must take place very rapidly.

In darkness and under many conditions in which an accident may have taken place, it is very difficult even for a skilled operator to observe when natural breathing has started and in consequence the necessary change over from one face mask to another may not be made at the necessary instant and this can lead to a failure of natural breathing and possibly to death which might have been prevented had natural breathing been maintained.

The aim of the present invention is to provide a lung ventilator which will provide ventilation by the intermittent supply to a face mask of respirable gas under pressure, but which will also provide a supply of gas to the same face mask upon demand if natural breathing is present or starts and then automatically change back to ventilation should natural breathing cease. The ventilator in accordance with the invention thus has great advantages over a conventional ventilator which will provide only ventilation and not allow for natural breathing, and permits operation by a medically unqualified operator as may be necessary, for example, in a mine, and also enhances the restoration and maintenance of natural breathing.

To this end, according to this invention, a lung ventilator includes a reservoir having two inlets, which lead to an inlet connection for a supply of respirable gas, and two outlets, which lead to a face mask connection for a face mask having a face valve, a first one of the inlets communicating with the inlet connection through a first flow regulator which provides the required minimum minute volume of gas flow for ventilation, the second inlet communicating with the inlet connection through a first valve device which opens when the pressure in the reservoir falls below a predetermined minimum value, a first one of the outlets communicating with the face mask connection through a second flow regulator and a second valve device, which is controlled by timing means which causes the second valve device to provide an intermittent flow of gas for ventilation, the second outlet communicating with the face mask connection through a demand valve, and means being provided which prevents the second valve device from allowing any flow of gas to the face mask connection when the pressure in the reservoir is below a predetermined value and which causes the intermittent flow of gas through the second valve device to be resumed to provide ventilation when the pressure in the reservoir rises above a predetermined maximum value.

To use the lung ventilator in accordance with the invention, oxygen or other respirable gas under pressure is supplied to the inlet connection and a face mask with a face valve, which is connected to the face mask connection, is applied to the face of the person whose lungs may require to be ventilated. It is not, however, necessary for the operator to know whether ventilation is necessary or whether the person is breathing naturally, since gas will be supplied by the ventilator to the face mask to meet either requirement. If natural breathing is not taking place, ventilation will automatically take place, but if natural breathing is taking place, then there will be a demand supply of gas to the face mask through the demand valve. As natural breathing through the demand valve will generally call for a greater supply of gas than that provided by the first flow regulator, a drop in pressure in the reservoir will take place and accordingly the first valve device will open to provide a further supply of gas to the reservoir through the second inlet.

If natural breathing is initially absent or ceases, no gas will be drawn through the demand valve and the pressure in the reservoir will rapidly be raised by the supply of gas through both inlets. As soon as this pressure reaches the predetermined maximum value, the second valve device will allow gas to flow through it and the timing means will be set in operation to cause gas to be supplied intermittently to the face mask through the second flow regulator which provides gas at the required inspiratory rate of flow. The use of the pressure in the reservoir to control both the supply of gas to the reservoir and also the supply of gas from the reservoir to the face mask makes it possible to use gas pressure-operated valve devices and the entire ventilator can be made very simply.

Whilst the timing means may be operated electrically, or by clockwork, in one example, it is gas-pressure operated and is actuated by the supply of respirable gas to the face mask. In this example, the second valve-device is a spool valve which is operated in one direction by the supply of respiratory gas under pressure against the action of a spring. The supply of gas under pressure opens the spool valve and the spring closes the valve when the supply of respiratory gas to a control port of the spool valve is discontinued. The gas supplied to the control port of the valve is vented to atmosphere and is not used for respiration.

The supply of gas for opening the spool valve between the first outlet of the reservoir and the face mask is preferably controlled by a YES unit, the control of which communicates with the first outlet of the reservoir in which the pressure rises as the reservoir pressure increases to trigger the YES unit when the predetermined maximum pressure is reached. To provide the intermittent triggering of the YES unit to open and close the spool valve and so provide the intermittent gas supply for ventilation, an auxiliary gas reservoir may be provided in the connection to the control part of the YES unit. This auxiliary reservoir is charged with gas supplied at a low rate through the second flow regulator which provides only the inspiratory flow and this charging takes place while the spool valve is closed. When the spool valve is opened, the pressure on the downstream side of the second flow regulator decreases to the lung pressure of the person being ventilated and this causes the pressure in the auxiliary reservoir to decay slowly through a further flow regulator and, when it has decayed below the triggering pressure of the YES unit, the YES unit closes and vents the supply of gas to the spool valve so that the spring closes the valve. The pressure in the auxiliary reservoir is then built up again by the flow of gas through the second flow regulator and this inflow takes place through a non-return valve which by-passes the further flow regulator which controls the decay of pressure in the auxiliary reservoir.

For certain purposes, the example just described can be simplified. In particular, the spool valve can be replaced by a simpler valve device and the intermittent opening and closing of the simpler device may be controlled by the rise and fall of the pressure of the gas in the main reservoir without an auxiliary gas reservoir being necessary.

In this simplified example, the second valve device is preferably a YES unit and the timing means then comprises a second YES unit which controls a supply of gas from the inlet connection to the control of the first YES unit. Control of the second YES unit, which corresponds to the YES unit which operates the spool valve in the first example, has its own control connected to the reservoir.

Thus when the pressure in the main reservoir is above a predetermined value, the second YES unit is triggered to supply gas to the control of the first YES unit so that this is also triggered and the gas is supplied to the face mask connection. The rate of supply of gas to the reservoir through the first flow regulator is less than the rate of flow of gas from the regulator to the second flow regulator and accordingly the pressure in the main reservoir falls until after a time interval the second YES unit closes and this in turn closes the first YES unit, after which the pressure in the reservoir starts to rise again. The second YES unit is of course arranged to close before the pressure in the reservoir falls to the predetermined minimum value at which the first valve device opens and additional gas is supplied to the reservoir of the second inlet.

When the second YES unit is provided, this also forms the means which prevents the second valve device, that is the first YES unit, from allowing any flow of gas through it to the face mask connection when the pressure in the main reservoir is below a predetermined value and causes the intermittent flow of gas through the second valve device to be resumed to provide ventilation wen the pressure in the main reservoir rises above a predetermined maximum value. In this case the predetermined maximum value of the pressure is equal to the predetermined value at which the second YES unit is triggered and the predetermined value of the pressure below which the second valve device is prevented from allowing any gas flow to the face mask connection is equal to the pressure at which the second YES unit closes.

In both the examples just described, the first valve device controlling the supply of gas through the second inlet to the main reservoir preferably comprises a NOT unit and a non-return valve and the NOT unit is controlled by a pressure connection to the main reservoir. In the first example, the NOT unit is triggered in a conventional manner, to shut off the supply to the main reservoir when the pressure in this reservoir rises above a further predetermined value and the YES unit which controls the spool valve is triggered to shut off the supply of gas to the control port of the spool valve to close the spool valve when the pressure in the second outlet from the main reservoir falls below another predetermined value.

Two examples of ventilators in accordance with the invention will now be described with reference to the accompanying drawings, in which.

Figure 1:
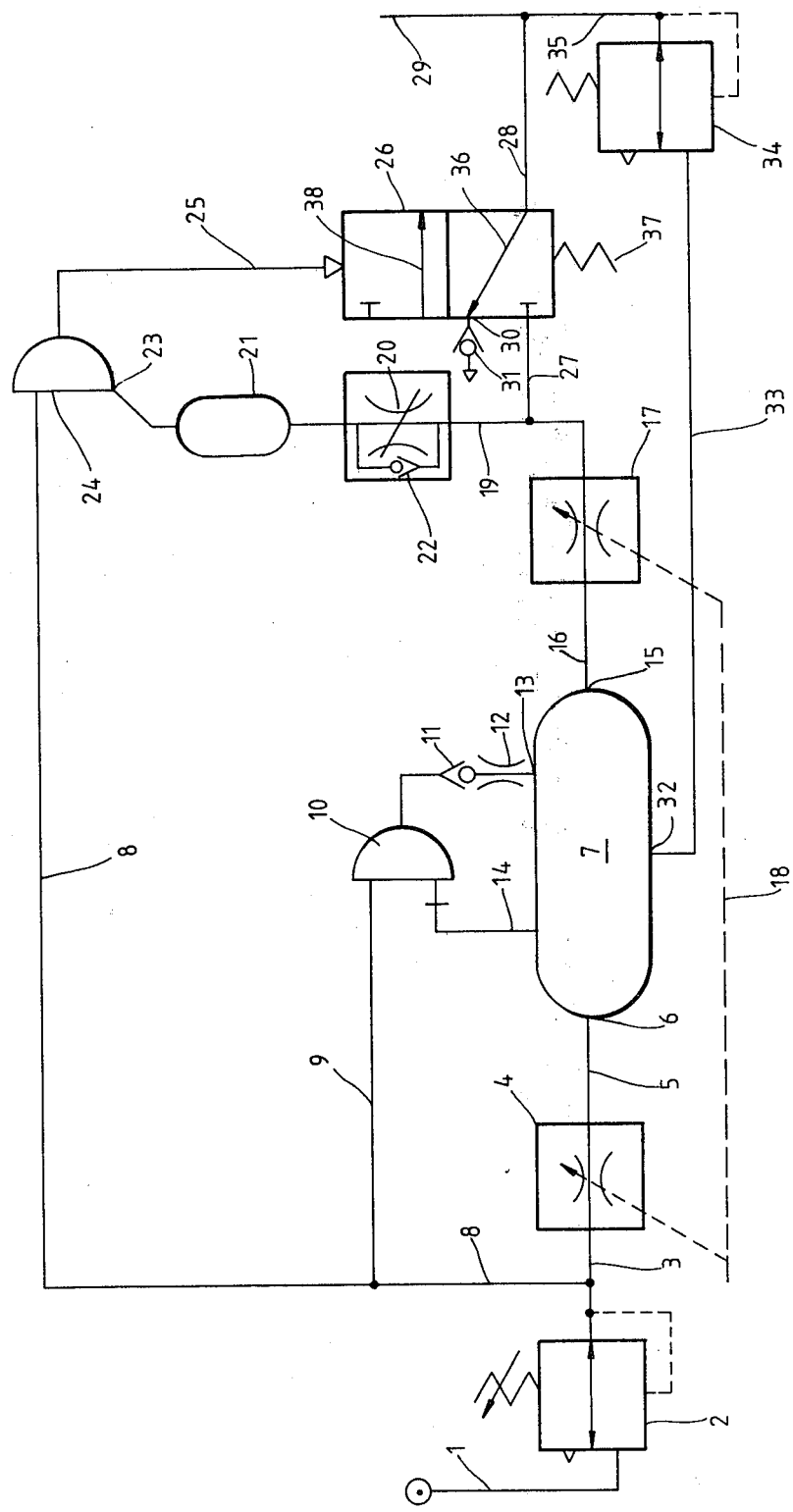
FIG. 1 is a pneumatic circuit diagram of a first example.
Figure 2:
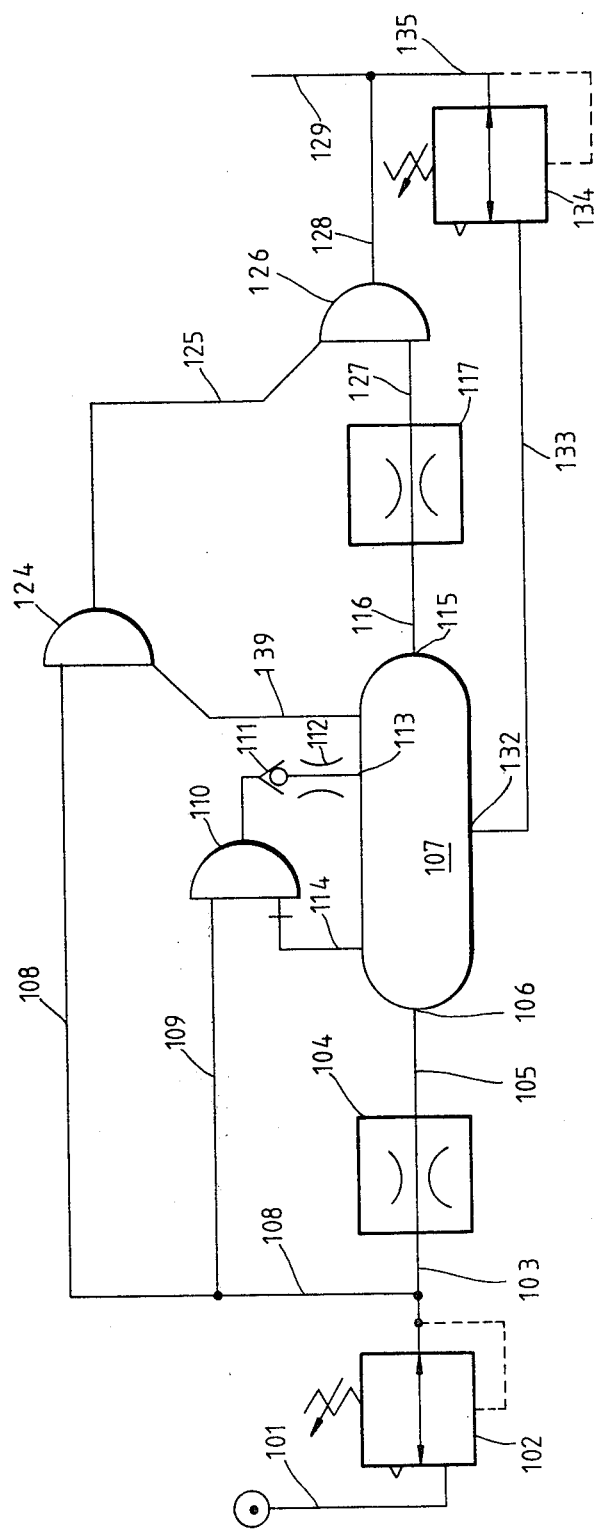
FIG. 2 is a pneumatic circuit diagram of a second, simplified example.

In the first example, oxygen is supplied from a cylinder through a line 1 at a pressure of from 4 to 7 bar. to a pressure regulator 2, which in this example is set to deliver a steady pressure of 4 bar. The pressure regulator 2 is connected by a line 3 to a variable flow regulator 4. The flow regulator 4 can be varied to provide the required minimum minute volume gas flow for an adult, child or baby. The flow from the regulator 4 passes through a line 5 to a first inlet 6 of a reservoir 7. A further line 8 leads from the line 3 to a line 9 which is connected to the inlet of a NOT unit 10. The outlet of the NOT unit 10 is connected to a non-return valve 11 and thence through a flow restrictor 12 to a second inlet 13 of the reservoir 7. The control port of the NOT unit 10 is connected by a line 14 to the reservoir 7 so that the NOT unit is triggered by the pressure within the reservoir.

A first outlet 15 is connected by a line 16 to a second flow regulator 17 which is adjustable to provide inspiratory rate of flow for an adult, child or baby the inspiratory flow rate being greater than the minute volume flow rate provided by the regulator 4 and the control of the regulator 17 is connected mechanically to the control of the regulator 4 as indicated by the dotted line 18 so that both regulators can be adjusted manually.

A line 19 leads from the regulator 17 through a flow restrictor 20 to an auxiliary reservoir 21. The restrictor 20 is by-passed by a line with a non-return valve 22. An outlet of the auxiliary reservoir 21 is connected to a control port 23 of a YES unit 24. The inlet of the YES unit 24 is connected to the line 8 and the outlet of the YES unit 24 is connected by a line 25 to a pilot port of a pilot-operated three-way spool valve 26.

The spool valve 26, which forms a shut-off valve, has an inlet port connected by a line 27 to the line 19, an outlet port connected by a line 28 to a flexible tube 29 leading to a conventional face valve and mask, and a port 30 vented to atmosphere through a non-return valve 31.

A second outlet 32 of the reservoir 7 is connected by a line 33 to a demand valve 34, the outlet of which is connected by a line 35 to the tube 29 which leads to the face mask.

In operation, to resuscitate a person who is not breathing, the face mask is applied to the person, the regulators 4 and 17 are set according to whether the person is an adult, child or baby and the oxygen supply to the line 1 is turned on. Since at this stage the reservoir 7 is not pressurised, the NOT unit 10 is open and oxygen is supplied to the reservoir 7 through the first inlet 6 and through the second inlet 13. In this example the NOT unit 10 opens at a pressure of 9% of the reference pressure of 4 bar and closes at 40% of this pressure. Thus as soon as the reservoir 7 reaches a pressure of 1.6 bar, flow through the inlet 13 ceases, but the minute volume flow through the inlet 6 continues.

Initially no pressure is applied to the YES unit 24 through the control port 23 and accordingly the YES unit, which opens at 60% of the reference pressure of 4 bar and closes at 45% of the reference pressure is closed. Accordingly there is no pressure in the line 25 and the valve 26 adopts the porting indicated by the arrow 36 under the action of its spring 37. That is to say the valve 26 is closed to the flow through it of gas under pressure from the line 27, but the tube 29 is vented through the line 28 and the non-return valve 31.

The output from the regulator 17 flows through the line 19 and the non-return valve 22 and raises the pressure in the auxiliary reservoir 21 to that in the main reservoir 7. When this pressure reaches 60% of the reference pressure it causes the YES unit 24 to open and the supply of gas under pressure through the line 25 opens the valve 26 causing it to adopt the porting indicated by the arrow 38. Thus oxygen flows through the line 28 to the tube 29 and inflates the lungs of the person to whom the face mask is applied.

When the valve 26 opens, the pressure downstream of the regulator 17 decreases to the lung pressure of the person whose lungs are being ventilated and in consequence the pressure previously built up in the auxiliary reservoir 21 gradually decays through the restrictor 20 and when this pressure reaches 45% of the reference pressure, the YES unit 24 closes and vents the line 25 so that the valve 26 closes. The lungs of the person being ventilated thus emit gas through the face valve under their own elasticity. The cycle just described is then repeated and the lungs are alternately inflated and deflated. This state of affairs continues unless the person whose lungs are being ventilated starts to breathe of their own accord. When this happens, the flow of oxygen required during inhalation is likely to be greater than the flow through the regulator 17 and it is also likely that inhalation will take place while the valve 26 is closed. If this happens, the pressure on the outlet side of the demand valve 34 drops and the demand valve 34 opens so enabling the person whose lungs are being ventilated to inhale air through the line 35, the demand valve 34 and the line 33 directly from the reservoir 7.

The outflow from the reservoir through the line 33 is greater than the inflow through the regulator 4 and in consequence the pressure in the reservoir 7 falls. When the pressure falls to 9% of the reference pressure, the NOT unit 10 opens and the reservoir is supplied with additional oxygen through the line 9 and the non-return valve 11. The restrictor 12 is provided to ensure that the flow through the line 9 is not so great as to reduce the reference pressure acting through the line 8 on the YES unit 24.

There is thus an ample supply of oxygen to the person wearing the face mask and natural breathing can continue. During this natural breathing the pressure in the reservoir 7 and hence in the auxiliary reservoir 21 does not rise above 40% of the reference pressure and accordingly the YES unit 24 remains closed and so therefore also does the valve 26.

If, however, the person to whom the face mask is fitted ceases to breathe naturally, no further air will be taken through the demand valve 34 and in consequence the pressure in the reservoir 7 will start to rise owing to the continued inflow through the regulator 4 and the first inlet 6. The increase in pressure in the reservoir 7 is communicated to the auxiliary reservoir 21 and as soon as this pressure rises to 60% of the reference pressure, the YES unit 24 opens and this causes the valve 26 to open so that lung ventilation automatically starts again and continues in the manner already described until such time as natural breathing may start again.

In the second example, oxygen is supplied from a cylinder through a line 101, at a pressure of from 4 to 7 bar., to an adjustable pressure regulator 102 which, when the ventilator is used on an adult is set to deliver a steady pressure of 4 bar. The regulator 102 is connected by a line 103 to a flow regulator 104 which is in the form of a simple orifice of constant cross section, the cross section being of such a size that at the pressure of 4 bar it passes the required minute volume of flow of oxygen for an adult. The flow from the regulator 104 passes through a line 105 to a first inlet 106 of a reservoir 107. A further line 108 leads from the line 103 to a line 109 which is connected to the inlet of a NOT unit 110. The outlet of NOT unit 110 is connected to a non-return valve 111 and thence through a flow restrictor 112 to a second inlet 113 of the reservoir 107. The control port of the NOT unit 110 is connected by a line 114 to the reservoir 107 so that the NOT unit is triggered by the pressure within the reservoir.

A first outlet 115 is connected by a line 116 to a second flow regulator 117, which is again in the form of a simple orifice of a size such as to supply the required oxygen flow during the inspiratory part of a ventilation cycle. The flow through the regulator 117 is greater than that through the regulator 104.

A second outlet 132 from the reservoir 107 leads through a line 133 to a demand valve 134 which is connected by a line 135 to a flexible tube 129 which leads a conventional face valve and mask.

The parts of the ventilator so far described are the same as the corresponding parts of the first example except that the two fixed flow regulators 104 and 117 are provided in place of variable flow regulators in the previous example.

However, in place of the shut-off valve of the spool type which is provided in the example of the ventilator described in our prior Application, the regulator 117 is connected on its downstream side by a line 127 to the inlet of a first YES unit 126. The outlet of the YES unit 126 is connected by a line 128 to the flexible face mask tube 129.

The control port of the YES unit 126 is connected by a line 125 to the outlet of a second YES unit 124 which corresponds in its function to the YES unit 24 in the first example. The YES unit 124 has its inlet connected to an extension of the line 108 and its control port is connected by a line 139 to the reservoir 107 so that the YES unit 124 is triggered by the pressure in the reservoir 107. When triggered, oxygen is supplied from the line 108 through the second YES unit 124 and the line 125 to trigger the YES unit 126 so that oxygen can flow from the reservoir 107 through the regulator 117, the YES unit 126 and the line 128 to the face mask tube 129.

In operation, to resuscitate a person who is not breathing, the face mask is applied to the person and the oxygen supply to the line 101 is turned on. Since at this stage the reservoir 107 is not pressurised, the NOT unit 110 is open and oxygen is supplied to the reservoir 107 through the first inlet 106 and through the second inlet 113. The NOT unit 110 opens at a pressure of 9% of the reference pressure of 4 bar and closes at 40% of this pressure. Thus, as soon as the reservoir 107 reaches a pressure of 1.6 bar, flow through the inlet 113 ceases, but the minute volume flow through the inlet 106 continues. Initially no pressure is applied to the control port of the YES unit 124 through the line 139 and accordingly the YES unit 124, which opens at 60% of the reference pressure of 4 bar and closes at 45% of this pressure is closed. There is therefore no oxygen pressure in the line 125 and the first YES unit 126 is also closed.

When the pressure in the reservoir 107 reaches 2.4 bar, that is 60% of the reference pressure, the second YES unit 124 is triggered and this causes the line 125 to be pressurised so that the first YES unit 126 is triggered and oxygen can flow from the regulator 117 through the YES unit 126 to the face mask tube 129.

As already stated, the regulator 104 provides a substantially smaller flow than the regulator 117 and in consequence the pressure in the reservoir 107 starts to fall. The reservoir 107 is made of such a volume that after the required inspiratory time, the pressure in the reservoir 107 has fallen to 45% of the reference pressure and in consequence the second YES unit 124 is closed and this causes the first YES unit to be closed also. Consequently the supply of oxygen to the face mask tube 129 ceases.

The pressure in the reservoir 107 then starts to build up again as there is an inflow through the regulator 104, but no outflow and, when the pressure has increased from 45% of the reference pressure to 60% of the reference pressure, the YES units 124 and 126 are again triggered and a further cycle of operation of the ventilator ensues.

If during ventilation by the cycle of operations as described, the patient starts breathing, the demand valve 134 opens and the amount of oxygen breathed exceeds the minute volume flow through the regulator 104 and in consequence the pressure in the reservoir 107 falls. As soon as the pressure has fallen below 45% of the reference pressure, the YES units 124 and 126 close and remain closed so long as the pressure remains below 60% of the reference pressure. In fact the demand is such that the pressure in the reservoir 107 falls below 9% of the reference pressure and this causes the NOT unit 110 to be triggered so that further oxygen is supplied to the reservoir through the line 109 and the second inlet 113. However the NOT unit 110 closes again when the pressure in the reservoir 107 reaches 40% of the reference pressure and this is before the second YES unit 124 is triggered so that as long as the demand supply continues, the YES unit 126 remains closed.

If however the person to whom the face mask is fitted ceases to breathe, the demand valve 134 closes and therefore the pressure in the reservoir 107 starts to rise owing to the oxygen supply through the regulator 104 until once again the pressure reaches 60% of the reference pressure at which time the YES units 124 and 126 are again triggered and ventilation starts again in the manner already described.

If the ventilator is used on a child or baby who requires a smaller minute volume of flow for ventilation purposes, all that is necessary is to adjust the regulator 102 to deliver a lower reference pressure.

As will be appreciated by those familiar with pneumatic logic circuits, exactly the same operation can be obtained in the second example if the YES units 124 and 126 are substituted by NOT units which are triggered at the same percentages of the reference pressure.

It will be seen that in both of the examples, change-over from ventilation to natural breathing or vice versa takes place entirely automatically and at all times the supply of oxygen or other respirable gas is breathed without any contamination from the surrounding atmosphere without it being at any time necessary to remove the face mask from the face of the person on whom the ventilator is being used. This automatic change-over has not, as far as we are aware, ever been achieved before and particularly not with a simple entirely pneumatically controlled ventilator. A further advantage of the lung ventilator in accordance with the invention is that owing to the automatic change-over between ventilation and demand supply, the ventilator will automatically provide a guaranteed minimum minute volume of oxygen or other respirable gas to a person being resuscitated either by natural breathing or by artificial ventilation. If the person is naturally breathing a greater volume than this guaranteed minimum, then no artifical ventilation takes place. If breathing is present, but is inadequate, the ventilator provides the difference between the naturally breathed volume and the guaranteed minimum volume as artifical ventilation. If natural breathing is absent, then the full guaranteed minimum volume is provided by artificial respiration.

I claim:

1. A lung ventilator including a reservoir, first and second inlets to said reservoir, an inlet connection communicating with said inlets for a supply of respirable gas to said reservoir, first and second outlets from said reservoir, a face mask connection for a face mask having a face valve, means communicating said face mask connection with said first and second outlets, a first flow regulator connected between said first inlet and said inlet connection, said first flow regulator providing a predetermined minimum minute volume of gas flow for ventilation, a first valve device connected between said second inlet and said inlet connection, said first valve device being constructed to open when the pressure in said reservoir falls below a first predetermined value and to close when said pressure rises to a second predetermined value higher than said first predetermined value, a second flow regulator and a second valve device connected between said first outlet and said face mask connection, said second flow regulator providing an inspiratory flow rate which is greater than the flow rate provided by said first flow regulator, and said second valve device being downstream of said second flow regulator, timing means controlling said second valve device, said timing means being operative to cause said second valve device to provide an intermittent flow of gas for ventilation, a demand valve between said second outlet and said face mask connection, and means which is operative to prevent said second valve device from allowing any flow of gas from said first outlet to said face mask connection when the pressure in said reservoir is below a third predetermined value which is higher than said second predetermined value, and said means also being operative to cause said intermittent flow of gas through said second device to be resumed to provide ventilation when said pressure in said reservoir rises above a fourth predetermined value which is higher than said third predetermined value.

2. A ventilator as claimed in claim 1, and which said timing means is gas-pressure operated and includes actuating means which is operated by a supply of respirable gas to said face mask from said first outlet of said reservoir.

3. A ventilator as claimed in claim 2, in which said second valve device comprises a spool valve including a spool, means for supplying said respiratory gas under pressure to said spool valve to move said spool in one direction, spring means for moving said spool in an opposite direction, said movement of said spool by said supply of respiratory gas under pressure opening said spool valve and said spring closing said spool valve when said supply of respiratory gas under pressure is discontinued.

4. A ventilator as claimed in claim 3, further comprising a YES unit for controlling said supply of respiratory gas to said spool valve for moving said spool in said one direction, said YES unit including a control, means communicating said control with said first outlet of said reservoir whereby said YES unit is triggered when said predetermined maximum pressure is reached in said reservoir.

5. A ventilator as claimed in claim 4, further comprising an auxiliary reservoir between said first outlet and said control of said YES unit and means connecting said auxiliary reservoir to the downstream side of said second flow regulator, whereby said auxiliary reservoir is charged with gas supplied at a low rate through said second flow regulator while said spool valve is closed, and a further flow regulator connected to said auxiliary reservoir, the pressure in said auxiliary reservoir decaying through said further flow regulator when said spool valve is opened so that when said pressure in said auxiliary reservoir has decayed below the triggering pressure of said YES unit, said YES unit closes and vents said supply of respiratory gas to said spool valve and allows said spring to move said spool to close said spool valve.

6. A ventilator as claimed in claim 4, further comprising an adjustable pressure regulator between said inlet connection and said first flow regulator, said pressure regulator being operative to supply respirable gas at an adjustable reference pressure to said first flow regulator.

7. A ventilator as claimed in claim 6, in which said YES unit opens at 60% of said reference pressure and closes at 45% of said reference pressure.

8. A ventilator as claimed in claim 1, in which said second valve device is a first YES unit, said first YES unit having a control, and said timing means comprises a second YES unit which controls a supply of gas from said inlet connection through said control of said first YES unit, said second YES unit including a control and means connecting said control of said second YES unit to said reservoir whereby, when the pressure in said reservoir is above a predetermined value, said second YES unit is triggered to allow the supply of gas through said control of said first YES unit so that first YES unit is also triggered and gas is supplied from said first outlet of said reservoir to said face mask connection, the rate of supply of gas to said reservoir through said first flow regulator being less than the rate of flow of gas from said reservoir through said second flow regulator whereby said pressure in said reservoir falls until said second YES unit closes and causes said first YES unit to be closed, said second unit being adapted to close before said pressure in said reservoir falls to said predetermined minimum value at which said first valve device opens.

9. A ventilator as claimed in claim 8, further comprising an adjustable pressure regulator between said inlet connection and said first flow regulator, said pressure regulator being operative to supply respirable gas to said first flow regulator at a reference pressure which is adjustable.

10. A ventilator as claimed in claim 9, in which both said first YES unit and said second YES unit open at 60% of said reference pressure and close at 45% of said reference pressure.

11. A ventilator as claimed in claim 1, in which said first valve device comprises a NOT unit having a control, a non-return valve between said NOT unit and said reservoir and means connecting said control of said NOT unit to said reservoir.

12. A ventilator as claimed in claim 11, further comprising an adjustable pressure regulator between said inlet connection and said first flow regulator, said pressure regulator being operative to supply respirable gas to said first flow regulator at a reference pressure of which is adjustable.

13. A ventilator as claimed in claim 12, in which said NOT unit opens at 9% of said reference pressure and closes at 40% of said reference pressure.

14. A ventilator as claimed in claim 1, in which said first and second flow regulators are adjustable to provide predetermined rates of flow for an adult, a child or a baby.

* * * * *